US008998856B2

(12) United States Patent
Eggert et al.

(10) Patent No.: US 8,998,856 B2
(45) Date of Patent: Apr. 7, 2015

(54) HANDHELD MEDICAMENT INJECTION DEVICE WITH ILLUMINATED DOSE BUTTON

(75) Inventors: Ilona Eggert, Frankfurt am Main (DE); Shane Alistair Day, Warwickshire (GB); Daniel Thomas De Sausmarez Lintell, Warwickshire (GB); Steven Wimpenny, Leamington Spa (GB); Alasdair Mackellar, Crewe (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

(21) Appl. No.: 14/346,998

(22) PCT Filed: May 24, 2012

(86) PCT No.: PCT/EP2012/059759

§ 371 (c)(1), (2), (4) Date: Mar. 25, 2014

(87) PCT Pub. No.: WO2012/160166

PCT Pub. Date: Nov. 29, 2012

(65) Prior Publication Data

US 2014/0236093 A1 Aug. 21, 2014

(30) Foreign Application Priority Data

May 25, 2011 (EP) .................................... 11167540

(51) Int. Cl.
*A61M 5/00* (2006.01)
*A61M 5/19* (2006.01)
(Continued)

(52) U.S. Cl.
CPC ............. *A61M 5/19* (2013.01); *A61M 5/14546* (2013.01); *A61M 5/2448* (2013.01);
(Continued)

(58) Field of Classification Search
CPC ... A61M 5/19; A61M 5/2046; A61M 5/2448; A61M 5/31523; A61M 5/31546; A61M 2005/24; A61M 5/28; A61M 5/24; B05C 17/00553; B65D 83/68; A61C 5/064; A61C 9/0026
USPC ........... 604/191, 82, 192, 193, 194, 195, 256, 604/87, 88, 200, 187, 188, 519, 520, 232, 604/233, 234, 235; 222/145.5, 145.6, 222/325–327
See application file for complete search history.

(56) References Cited

U.S. PATENT DOCUMENTS 5,584,815 A * 12/1996 Pawelka et al. ............... 604/191
6,726,657 B1 * 4/2004 Dedig et al. ................. 604/152
(Continued)

FOREIGN PATENT DOCUMENTS

DE 102004053902 5/2006
EP 1561483 8/2005
(Continued)

OTHER PUBLICATIONS

International Search Report for Int. App. No. PCT/EP2012/059759, completed Aug. 22, 2012.
(Continued)

*Primary Examiner* — Bhisma Mehta
*Assistant Examiner* — Hamza Darb
(74) *Attorney, Agent, or Firm* — McDonnell Boehnen Hulbert & Berghoff LLP

(57) ABSTRACT

A cartridge holder is presented having a first cartridge retainer, at least a second cartridge retainer and a locking device for each cartridge retainer, wherein each cartridge retainer is configured to receive a medicament reservoir and wherein each cartridge retainer is movable between a closed and an open position, wherein the locking devices are configured to lock and unlock the cartridge retainers in the closed position and wherein the locking devices are configured to operate such that only one of the cartridge retainers at a time is movable into the open position. An apparatus is also presented that has a main body and a cartridge holder, wherein the cartridge holder is removably attached to the main body. A method for inserting of a medicament reservoir in a cartridge holder or in an apparatus is also described.

15 Claims, 12 Drawing Sheets

(51) Int. Cl.
*A61M 5/145* (2006.01)
*A61M 5/24* (2006.01)

(52) U.S. Cl.
CPC ...... *Y10T 29/49826* (2015.01); *A61M 2205/12* (2013.01); *A61M 2205/14* (2013.01); *A61M 2205/60* (2013.01); *A61M 2205/13* (2013.01); *A61M 2205/19* (2013.01); *A61M 2205/276* (2013.01); *A61M 2207/00* (2013.01)

(56) References Cited

U.S. PATENT DOCUMENTS

2003/0114798 A1* 6/2003 Langley et al. ............... 604/184
2004/0069044 A1 4/2004 Lavi et al.
2011/0201998 A1* 8/2011 Pongpairochana et al. .... 604/67

FOREIGN PATENT DOCUMENTS

WO 93/12828 7/1993
WO 2011/067187 6/2011

OTHER PUBLICATIONS

International Preliminary Report on Patentability for Int. App. No. PCT/EP2012/059759, mailed Dec. 5, 2013.

* cited by examiner 74
14
10
702
80
60
700
606
604
600
602
616
52
40
618
50
622
620
610
608
200
614
612
18

HANDHELD MEDICAMENT INJECTION DEVICE WITH ILLUMINATED DOSE BUTTON

CROSS REFERENCE TO RELATED APPLICATIONS

The present application is a U.S. National Phase Application pursuant to 35 U.S.C. §371 of International Application No. PCT/EP2012/059759 filed May 24, 2012, which claims priority to European Patent Application No. 11167540.1 filed May 25, 2011. The entire disclosure contents of these applications are herewith incorporated by reference into the present application.

TECHNICAL FIELD

The present patent application relates to medical devices of delivering at least two drug agents from separate reservoirs. Such drug agents may comprise a first and a second medicament. The medical device includes a dose setting mechanism for delivering the drug automatically or manually by the user.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

SUMMARY

The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable.

5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

In practical use of medical devices of the above mentioned type, it is required that the at least two medicament reservoirs, containers or cartridges are exchanged in certain periods. Empty or nearly empty reservoirs need to be replaced with filled reservoirs.

A precondition for the correct application of an above mentioned medical device is that the medicament reservoirs, containers or cartridges are inserted in the correct retainer of the medical device. Accordingly, the replacement of the medicament reservoirs has to be conducted with great care and high precaution of the respective user.

However, in practical use it may occur, that medicament reservoirs are inserted into the medical device in a wrong retainer. As a result, during application of the medical device the respective medicaments are dispensed in wrong doses. Such a misuse may lead to significant health threats.

The invention therefore faces the technical problem of reducing the risk of misuse of an above mentioned medical device and at the same time increasing its operability.

The technical problem is solved by a cartridge holder, which comprises a first cartridge retainer, at least a second cartridge retainer and a locking device for each cartridge retainer, wherein each cartridge retainer is configured to receive a medicament reservoir and wherein each cartridge retainer is movable between a closed and an open position, wherein the locking devices are configured to lock and unlock the cartridge retainers in the closed position and wherein the locking devices are configured to operate such that only one of the cartridge retainers at a time is movable into the open position.

By configuring the locking devices of the cartridge holder such that only one of the cartridge retainers at a time is movable into the open position, it is ensured that only one medicament reservoir at a time may be exchanged. Thus, the risk of confusion and wrong insertion of the respective medicament reservoir is reduced. Misuse of a medical device of the above mentioned type and therefore the occurrence of serious health threats are safely prevented.

Preferably, the locking devices are configured to operate between an openable condition, in which the respective cartridge retainer is movable into the open position, and a not-openable condition, in which the respective cartridge retainer is not movable into the open position.

The operation of the locking devices between an openable and a not-openable condition enables to move a cartridge retainer into an open position, while the other cartridge retainers are safely prevented from being opened. Thereby not only accidental opening of the false retainer is prevented but also any case of inadvertent opening by the user may be impeded. This allows for the medicament reservoirs to be exchanged in a specifically safe and institutional manner.

According to one preferred embodiment, the locking devices are locked and unlockable in the openable condition and locked but not-unlockable in the not-openable condition. In this sense the cartridge retainers are locked in the closed position and only unlocked for being moved into the open position. This ensures that the cartridge retainers safely remain in the closed position during use of the medical device. Undesired opening of the cartridge retainer and possibly the loss of medicament reservoirs is thereby prevented.

According to another embodiment, the locking devices are unlocked in the openable condition and locked in the not-openable condition. In this sense the cartridge retainers, during use of the medical device, may remain unlocked in their closed position and may only be locked temporarily while other cartridge retainers are opened in order to exchange the respective medicament reservoirs. Such an arrangement allows to realise the locking device with simple means and cost-effectively.

The above mentioned locking devices may preferably be configured to lock the cartridge retainers in a form-fitting and/or force-fitting manner. For the unlocking of the cartridge retainers, the form-fit and respectively the force-fit between the locking devices and the cartridge retainers may be released by any suitable mechanism.

Particularly simple to manufacture are locking devices in the form of latches, snap locks, spring bolts or the like. Likewise, the locking device may be provided as a locking mechanism that blocks a pivoting movement of the cartridge retainer in the region of its hinge. It is also conceivable to combine different locking mechanisms in order to provide the desired locking configuration in a specifically safe and reliable manner.

It is further preferred, that the locking devices are configured to operate from the openable into the not-openable condition and vice versa dependant on the positions of the cartridge retainers. In the same sense it is also conceivable, that each locking device is configured to operate dependant on the locking condition of the remaining locking devices.

Both configurations allow all locking devices to be operated only by a single user operation, in particular the unlocking of one locking device or the opening of the respective cartridge retainer. The operability of the cartridge holder is thereby facilitated.

Furthermore, the locking devices are configured to operate into the openable condition when all cartridge retainers are in the closed position. This ensures the cartridge retainers to be generally movable from the closed position into the open position in order to conduct an exchange of the respective medicament reservoir. As mentioned above, dependant on the type of the locking device chosen in each case, the locking device may in its openable condition be locked but unlockable or just unlocked.

It is moreover preferred, that the locking devices are configured to operate such that when one of the cartridge retainers is moved into the open position, the locking devices associated to the remaining cartridge retainers operate into the not-openable condition. In the same sense it is also conceivable, that each locking device is configured to operate such that when one of the locking devices is unlocked, the locking devices associated to the remaining cartridge retainers operate into the not-openable condition. As mentioned above, dependant on the locking device chosen in each case, the locking device is only locked or locked and not-unlockable in the not-openable condition.

Accordingly, in case one locking device is unlocked and/or the respective cartridge retainer is opened, the remaining locking mechanisms operate self-acting into the not-openable condition. Therefore, while the opened cartridge retainer remains open, the opening of any other cartridge retainer is safely impeded.

According to a further advantageous embodiment, a control device is provided, which is configured to determine the positions of the cartridge retainers. Likewise the control device may be configured to determine the locking condition of the locking devices. The determination of the cartridge retainer positions or the locking device conditions contributes to an increased operational reliability of the cartridge holder.

A particularly high degree of operational safety and reliability may be achieved when the control device is configured to operate the locking devices dependant on the position of the cartridge retainers. Accordingly, in a specifically simple manner the control device may be configured to operate the locking devices in an openable condition when all cartridge receivers are moved into the closed position. Likewise, the control device may be configured to operate the locking devices, such that when one of the locking devices is unlocked and/or the respective cartridge retainer is moved into the open position, the locking devices associated to the remaining cartridge retainers are operated into the not-openable condition.

It is especially advantageous if the control device is an electronic control unit. This allows the control unit not only to operate the locking devices dependant on the position of the cartridge retainers and/or the locking condition of locking devices, but to provide further functions to the user of the cartridge holder and the medical device respectively.

Such an electronic control unit may comprise at least an evaluation unit, which is configured to receive signals from a sensor unit. In this configuration the sensor unit may be an electronic or an electromechanical sensor, which is configured to send signals to the evaluation unit dependant on the positions of the cartridge retainers and/or the locking conditions of the locking devices. There may also be a sensor unit, which is configured to send signals to the evaluation unit dependant on the correct insertion of the medicament reservoirs. There may further be a sensor unit, which is configured to send signals to the evaluation unit dependant on the filling level of the medicament reservoirs. The sensor units and the evaluation unit may also be one component.

Further, the control unit preferably comprises a control panel with input means, such as buttons or the like, as well as output means, such as a digital display or a sound unit or the like. The input means may be configured to receive inputs from a user, whereas the output means may be configured to indicate information to the user. The digital display may be configured to show if a cartridge retainer is open and which medicament reservoir, filled with what type of medicament, has to be inserted into the opened cartridge retainer. Likewise the digital display and the sound unit may be configured to indicate if a medicament reservoir has not properly been inserted into the respective cartridge retainer. The output means may further be configured to indicate information concerning the filling level of the medicament reservoirs.

In a specifically cost-effective manner, the control device may also be a mechanical control device. Such a mechanical control device may be configured to mechanically interact with the locking devices. It is likewise conceivable, that a mechanical control device is configured to operate the locking devices between an openable and a not-openable condition dependant on the positions of the cartridge retainers.

In a further preferred embodiment, the first cartridge retainer is configured for receiving medicament reservoirs of different sizes and/or different geometrical shapes than the at least second cartridge retainer. In particular, the medicament reservoirs may differ in length or diameter. Likewise the medicament reservoirs may have different geometrical shapes such as square, hexagonal, or any other shaped profiles.

The configuration of the cartridge retainers with respect to size and geometrical shape of the respective medicament to be received ensures in a reliable and riskless manner, that the correct reservoir is inserted into the correct retainer. Due to geometrical restrictions it may be prevented that a large sized reservoir is inserted into a retainer configured for a small sized reservoir. Even if a small sized reservoir may be inserted into a retainer configured for a large size reservoir, the misuse of the cartridge holder is still avoided, since the user obviously recognizes the false size of the reservoir.

Further a cartridge detect switch may be provided in each retainer. The cartridge detect switches may be configured to detect the insertion condition of the respective medicament cartridges and/or the closing condition of the cartridge retainers. For example, the cartridge detect switch in the larger retainer may be positioned in such a way that a smaller cartridge is not detected, even when the cartridge retainer is in the closed position. Thus, only a cartridge with the right size is detected. In this way, safety for the user can be improved by preventing wrong insertion of the cartridges.

A lack in fit between retainer and reservoir may as already mentioned above also be detected by an electronic or electromechanical sensor unit, which is configured to send a signal to the evaluation unit dependant in the fitting condition between retainer and reservoir.

According to a further embodiment of the cartridge holder, the cartridge retainers are hinged to a cartridge housing and rotatable between the closed and the open position. On the one hand the opening and closing of the cartridge retainers may thereby easily be conducted. Furthermore, this allows the cartridge holder to be manufactured of a small number of parts. However, it is also possible for the cartridge retainers to be guided in the cartridge housing in a linear guide.

A cartridge holder according to the invention may in a particular advantageous manner be deployed in an apparatus, which furthermore comprises a main body, wherein the cartridge holder is removably attached to the main body. Such an apparatus may be a medical device, in particular a medical device for delivering more than one medicament from separate reservoirs. Since the cartridge holder is removably attached to the main body of the apparatus, the cartridge holder and the main body may be easily assembled. At the same time the cartridge holder may be exchanged entirely.

Furthermore, such an apparatus may comprise a dispense interface, which may removably be attached to the cartridge holder. The dispense interface may be configured such that an opening of the cartridge retainers is not possible, while the dispense interface is connected to the cartridge holder. Thereby, it is ensured that none of the cartridge retainers is opened unintentional, for example during use of the medical device. The dispense interface is preferably configured to receive a dose dispenser, such as a double ended needle assembly.

Furthermore, a sensor unit may be provided, which is configured to determine the attachment of the dispense interface to the cartridge holder and which is configured to send a corresponding signal to the evaluation unit. The control unit may in this case be configured to operate the locking devices dependant on the signal referring to the attachment condition of the dispense interface.

In a preferred embodiment, the control device, in particular the electronic control unit, is arranged on the main body of the apparatus. Thereby a particular good accessibility of the control device, especially of its input and output means, is ensured, whereby finally the operability of the medical device is improved.

The technical problem is furthermore solved by a method for inserting of medicament reservoirs in a cartridge holder according to the invention or an apparatus according to the invention.

The inventive method may involve the following steps:

1. Opening of a cartridge retainer.

2. Operating the locking devices associated to the remaining cartridge retainers into a not-openable condition.

3. Inserting the medicament reservoir in the opened cartridge retainer.

4. Closing of the opened cartridge retainer.

5. Operating the locking devices associated to the remaining cartridge retainers into an openable condition.

By implementing this method, it is guaranteed that only one of the cartridge retainers at a time is opened. While one cartridge retainer is in an open condition all further retainers are safely prevented from being opened as well. Thus, it is only possible to insert one medicament reservoir at a time into the cartridge holder or the apparatus respectively, whereby the risk of confusion, especially false insertion of a reservoir, is reduced.

In a preferred embodiment, the method steps may be conducted subsequently for at least two cartridge retainers. Accordingly, a medicament reservoir is first inserted into a first cartridge retainer and consecutively a further medicament reservoir is inserted into a second cartridge retainer. This allows an easy and safe insertion of medicament reservoirs in all cartridge retainers.

According to a further preferred embodiment of the invention, an empty medicament reservoir is removed from the opened cartridge retainer before the medicament reservoir is inserted in the cartridge retainer. Since such an exchange of a medicament reservoir generally bears an increased risk of confusion due to an increased number of reservoirs to be handled, this embodiment particularly allows a safe exchange of medicament reservoirs in an inventive cartridge holder or an inventive apparatus respectively.

BRIEF DESCRIPTION OF THE FIGURES

These as well as other advantages of various aspects of the present invention will become apparent to those of ordinary skill in the art by reading the following detailed description, with appropriate reference to the accompanying drawings, in which.

DETAILED DESCRIPTION

Figure 1:
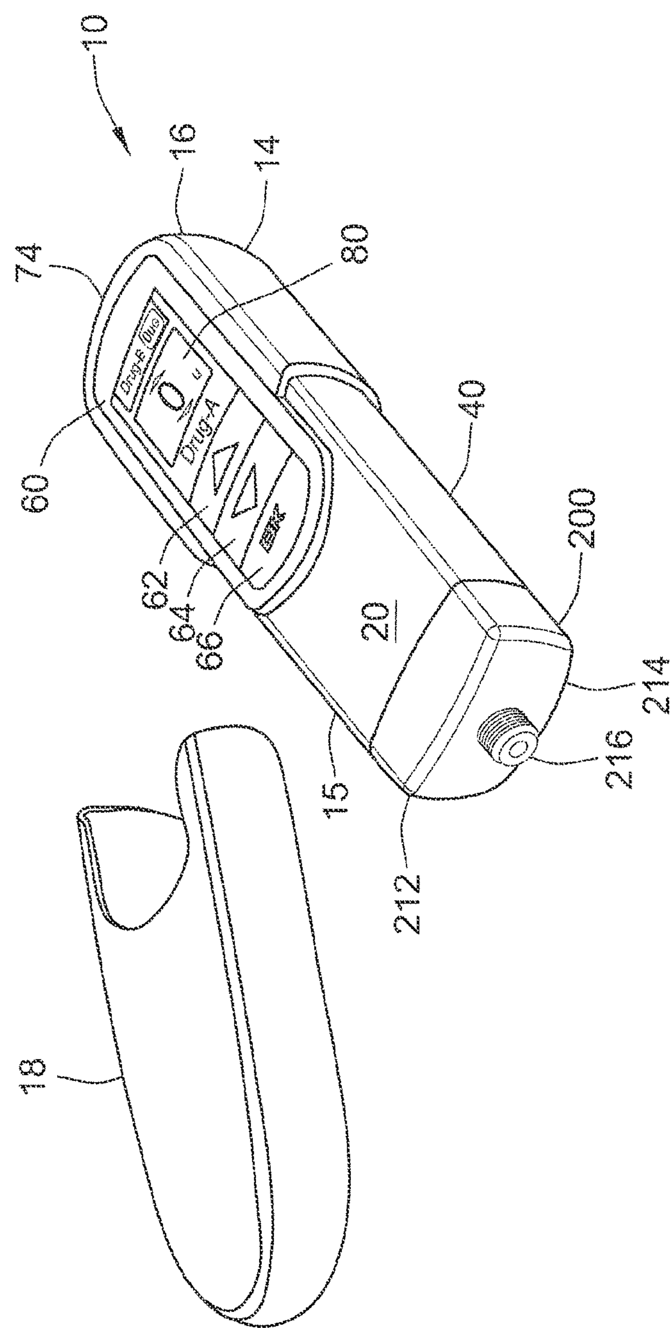
FIG. 1 illustrates a perspective view of the delivery device illustrated in FIGS. 1*a* and 1*b* with an end cap of the device removed.
Figure 2:
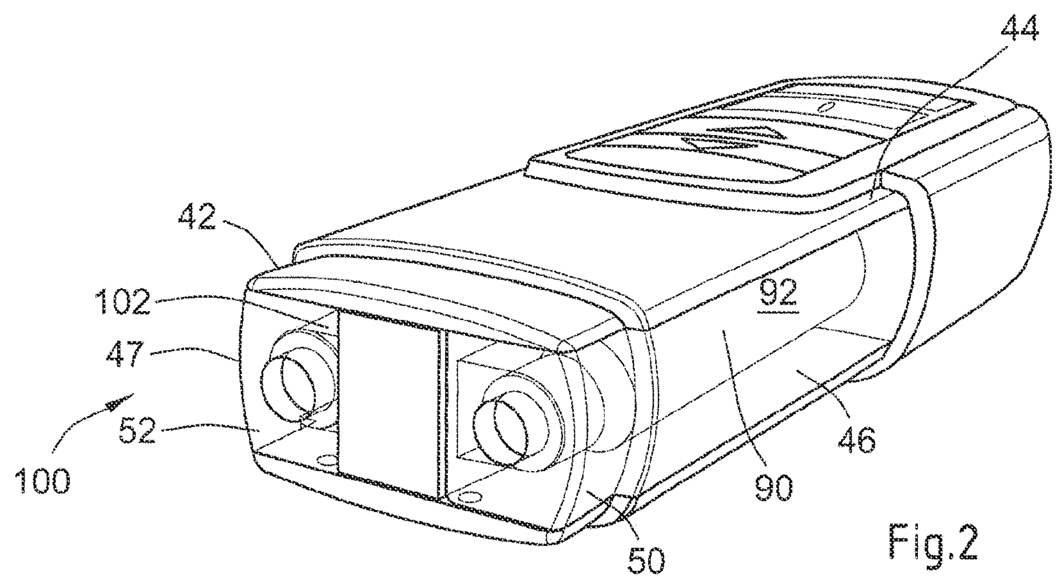
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK". In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
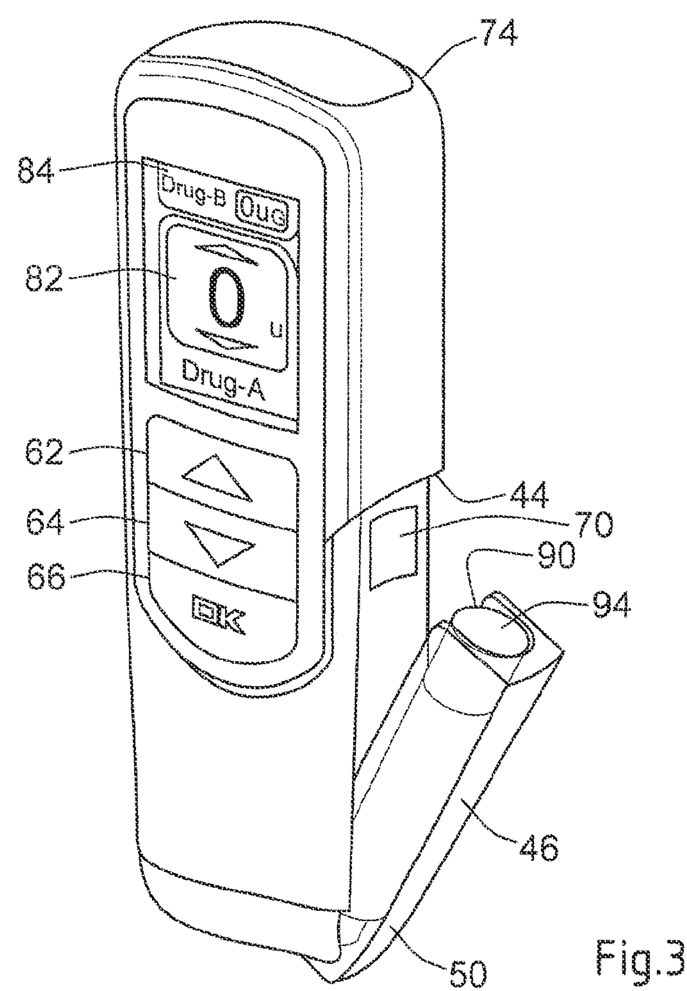
FIG. 3 illustrates a perspective view of the cartridge holder illustrated in FIG. 1 with one cartridge retainer in an open position.

As shown in FIG. 3, the first and a second cartridge retainers 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
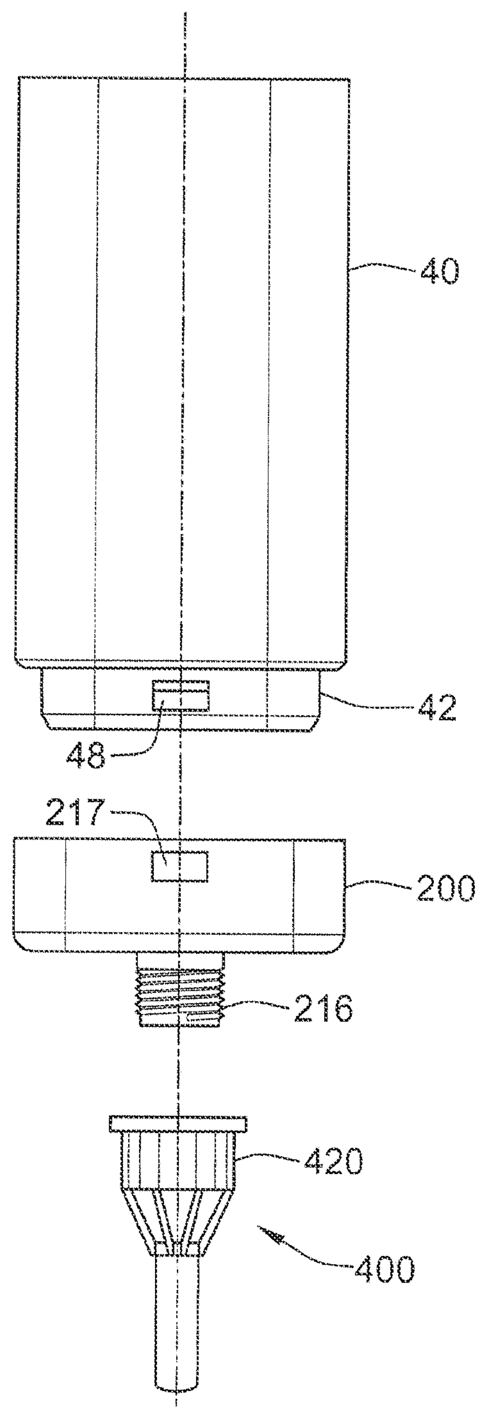
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
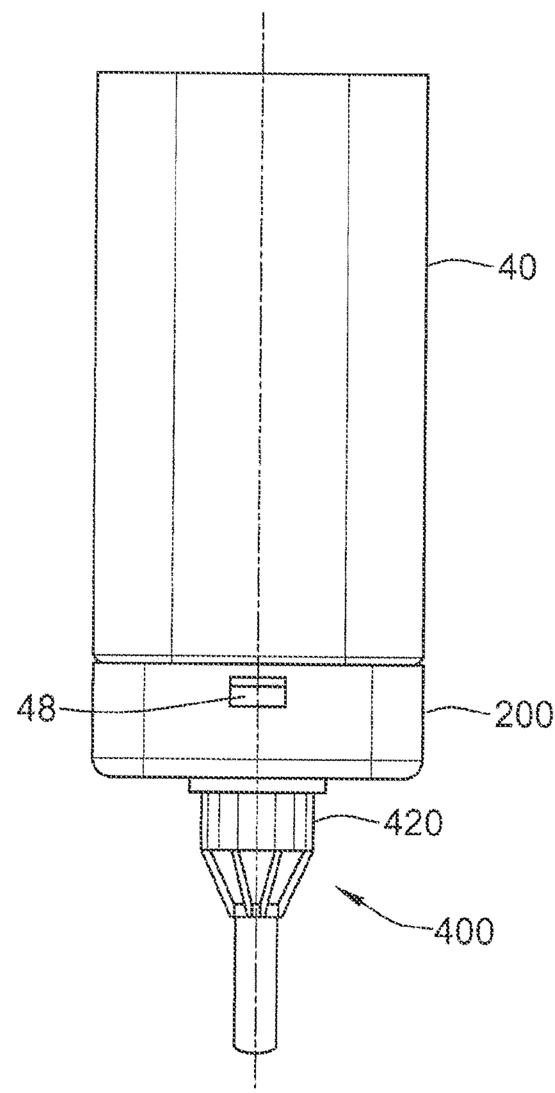
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
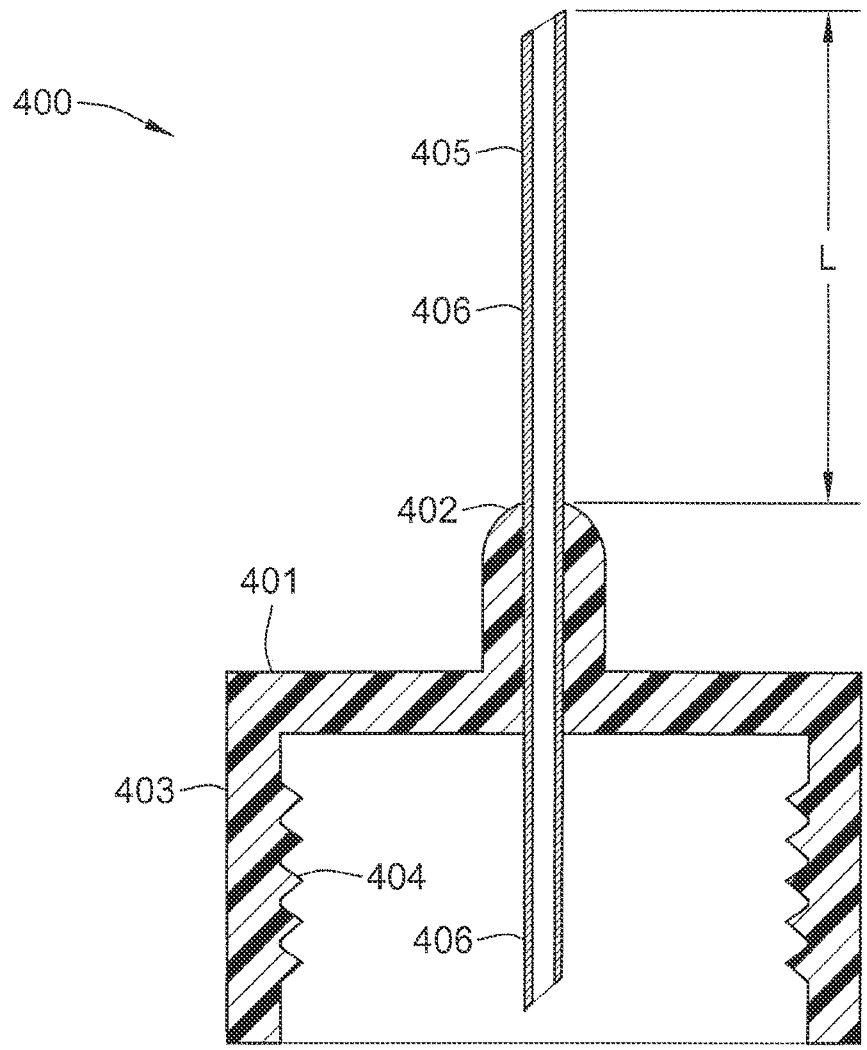
FIG. 6 illustrates one arrangement of the dose dispenser that may be mounted on a distal end of the delivery device.
Figure 7:
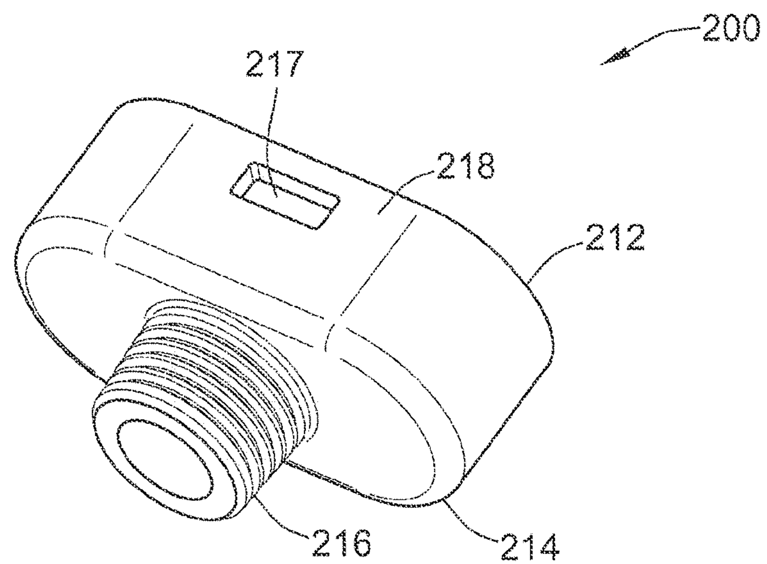
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib **213*a* and a second rib 213*b*. This first rib 213*a* is also illustrated in FIG. 10. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220**.

Figure 8:
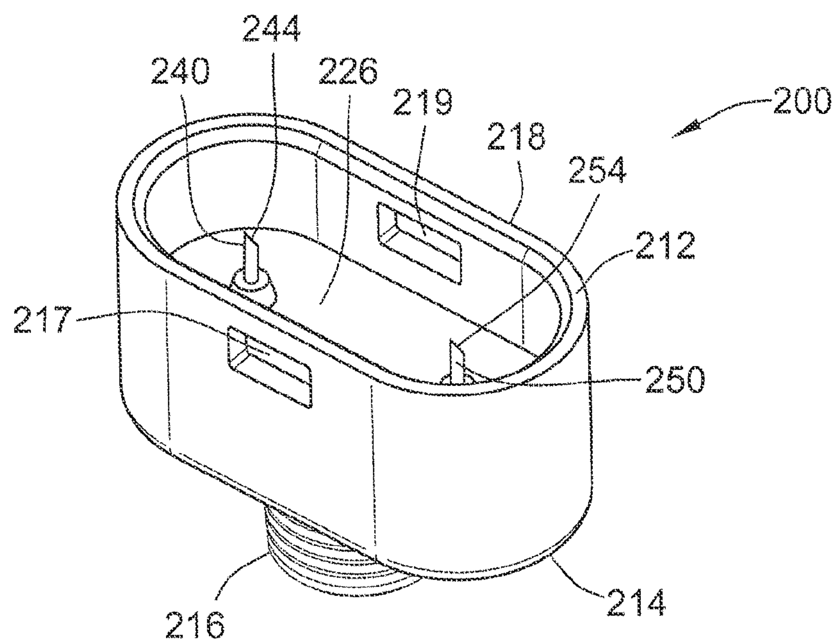
FIG. 8 illustrates another perspective view of the dispense interface illustrated in FIG. 4.
Figure 9:
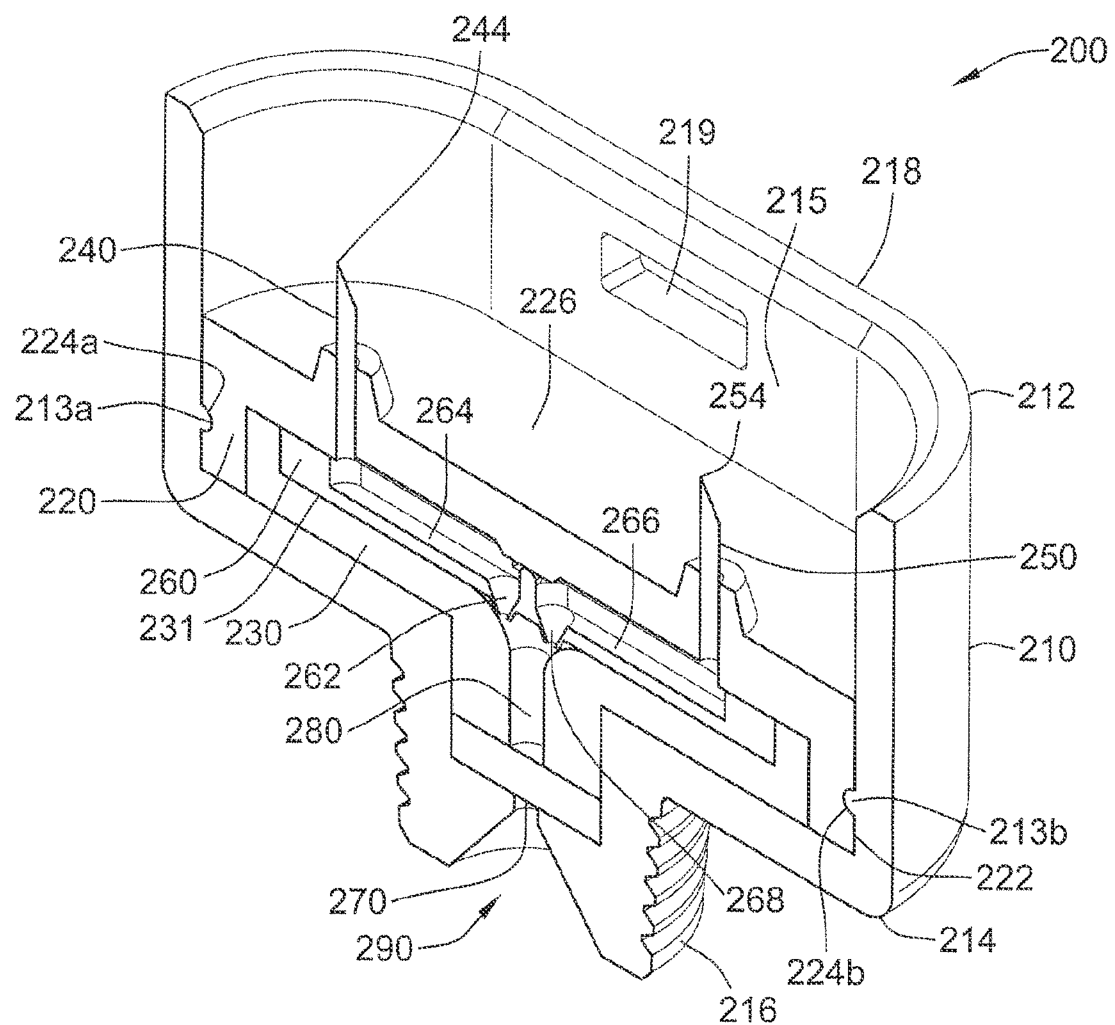
FIG. 9 illustrates a cross-sectional view of the dispense interface illustrated in FIG. 4.
Figure 10:
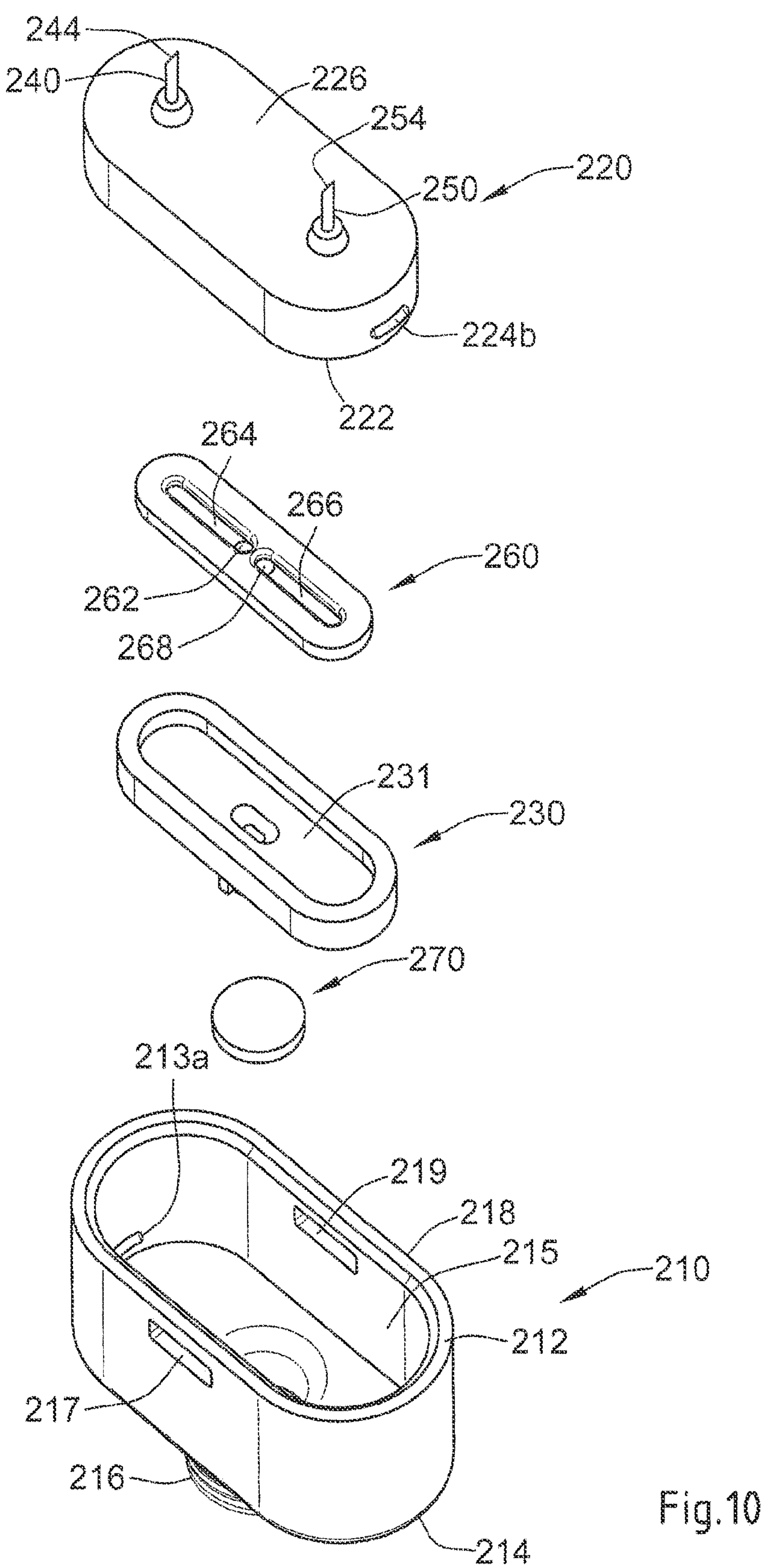
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
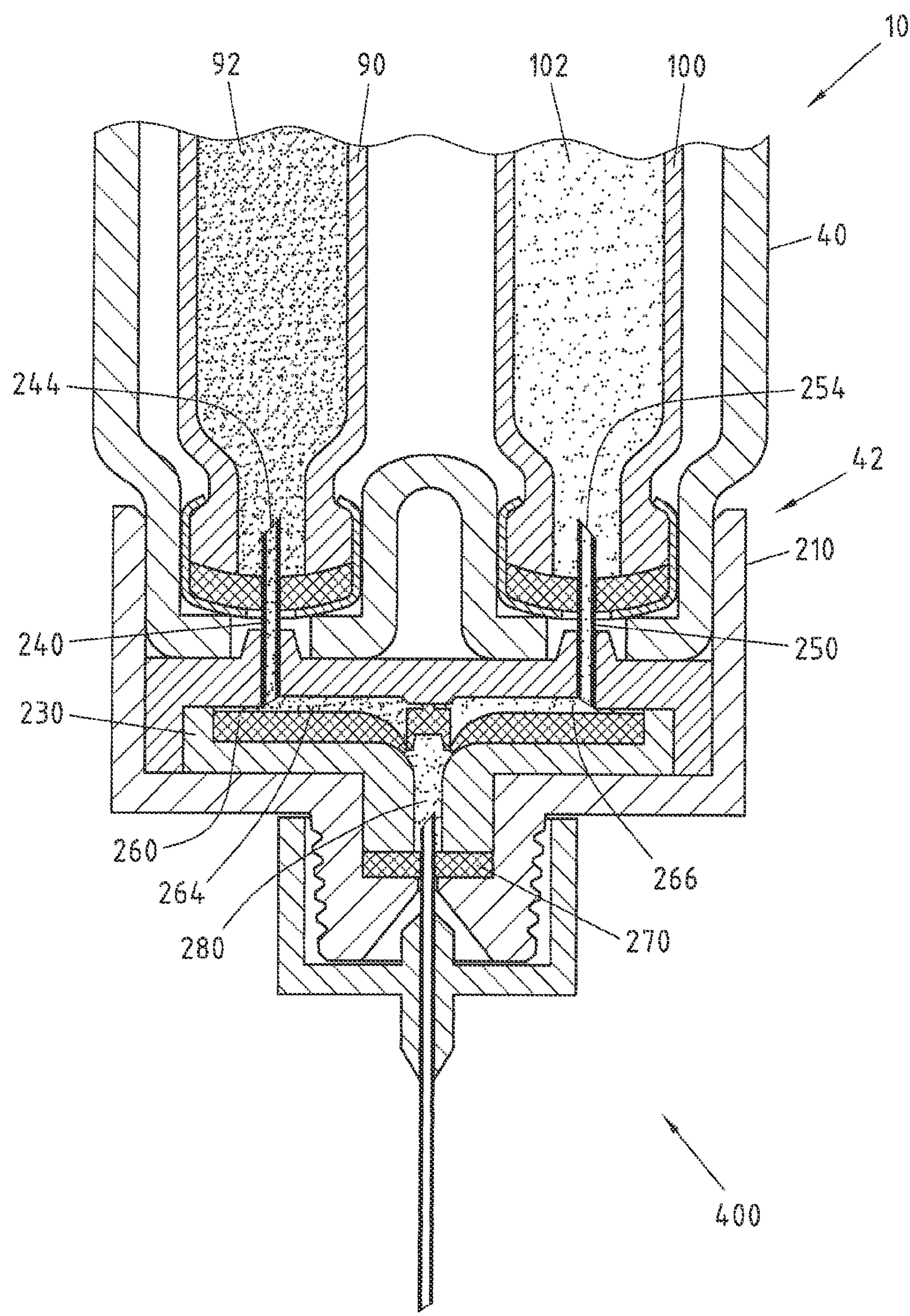
FIG. 11 illustrates a cross-sectional view of the dispense interface and dose dispenser mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
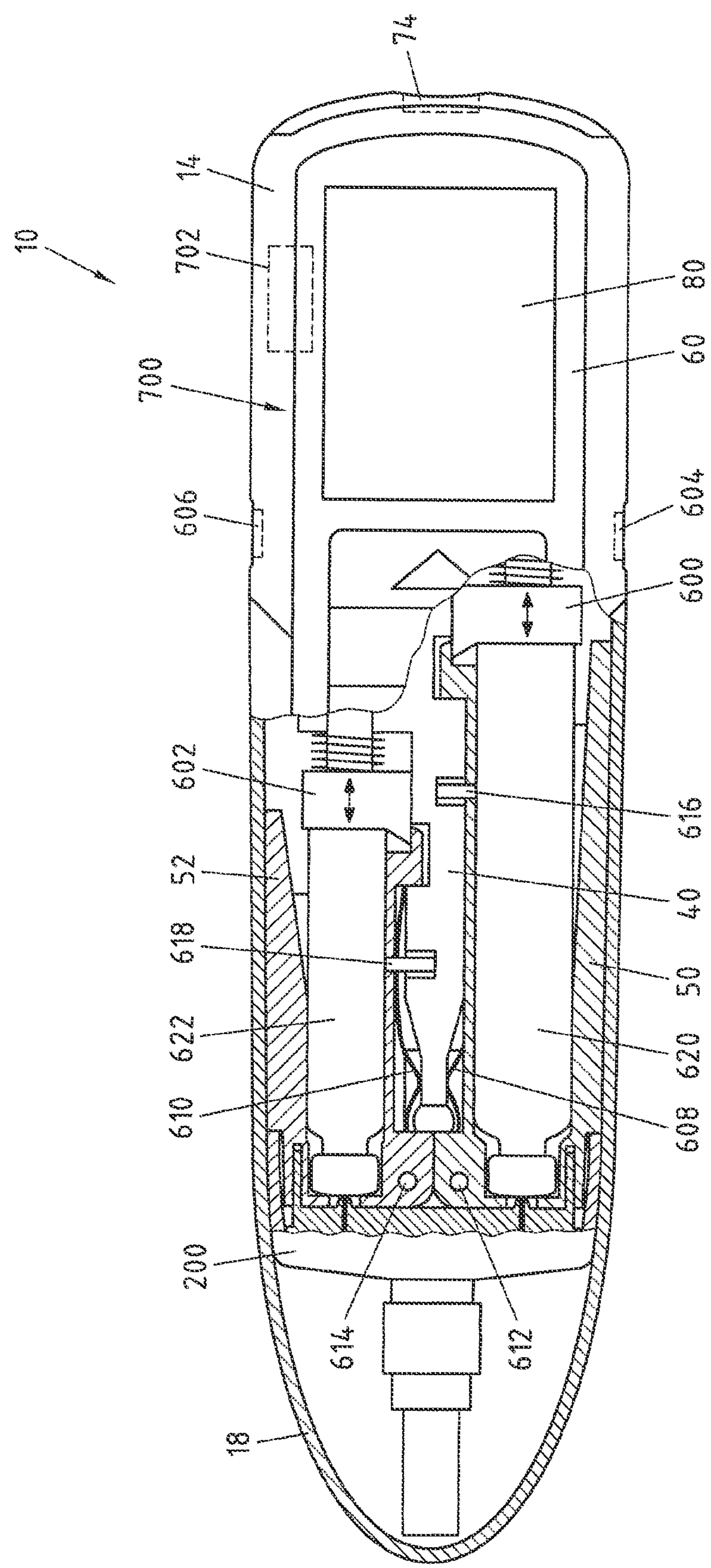
FIG. 12 illustrates a cross-sectional view of the medical device.

FIG. 12 illustrates a medical device 10 in cross sectional view. The medical device 10 comprises a cartridge holder 40, which is removably attached to a main body 14 of the medical device 10. A removable end cap or cover 18 is provided, which may be slid onto the distal end 15 of the main body.

The cartridge holder 40 may contain at least two cartridge retainers 50 and 52, which in FIG. 12 are illustrated in the closed position. Retainer 50 is configured so as to contain medicament reservoir 620, whereas retainer 52 is configured so as to contain medicament reservoir 622. The reservoirs 620,622 may be glass, metal or plastic cartridges. Reservoir 622 may have a smaller diameter and a shorter length than reservoir 620.

The cartridge holder 40 may further comprise two locking devices 600 and 602. The locking devices 600 and 602 may be designed as latches, which may lock the cartridge retainers 50,52 in a form-fitting manner in their closed position.

The locking devices 600 and 602 may be released or unlocked by operation of the cartridge release buttons 604 and 606. The cartridge release buttons 604 and 606 may work mechanical or electromechanical.

The locking devices 600 and 602 may further be controlled to unlock the cartridge holder only after a piston rod pushing a bung of the cartridge has been retracted from the cartridge. Thus, breaking or damaging the piston rod when exchanging the cartridge can be avoided.

The cartridge holder 40 further contains two cartridge retainer springs 608 and 610, which in the closed position of the cartridge retainers 50 and 52 exert an elastic spring force on the cartridge retainers. By releasing the locking devices 600 and 602 the spring force causes the cartridge retainers 50 and 52 to move in the open position.

Cartridge retainer 50 is hinged to the cartridge holder housing at pivot bearing 612, whereas cartridge retainer 52 is hinged to the cartridge holder housing at pivot bearing 614. The cartridge retainers 50,52 are thereby pivotable about the pivot bearings 612,614 between their closed and their open position.

The cartridge holder 40 may also comprise cartridge detect switches 616 and 618. The cartridge detect switches 616 and 618 may be configured to detect the insertion condition of the respective medicament cartridges 620,622 and/or the closing condition of the cartridge retainers 50 and 52. For example, cartridge detect switch 616 may be positioned in such a way, that a smaller cartridge, for example cartridge 622, is not detected in the larger cartridge retainer 50. Thus, only a cartridge with the right size is detected when the cartridge retainer is in the closed position.

The apparatus 10 further comprises a control device 700, which may be a micro-processor control unit. The control device 700 may comprise an evaluation unit 702, which may be configured to receive signals from the cartridge detect switches 616 and 618. The evaluation unit 702 may also be configured to receive signals from sensors that are configured to determine the filling level of the cartridges 620,622.

Furthermore, the control unit 700 preferably comprises a control panel region 60. Preferably, the control panel region 60 comprises output means such as a digital display 80 and input means such as dose setting buttons 62 and 64 or a button 66 designated with the symbol "OK". At the proximal end of the main body 14, further an injection button 74 is provided.

Figure 13B:
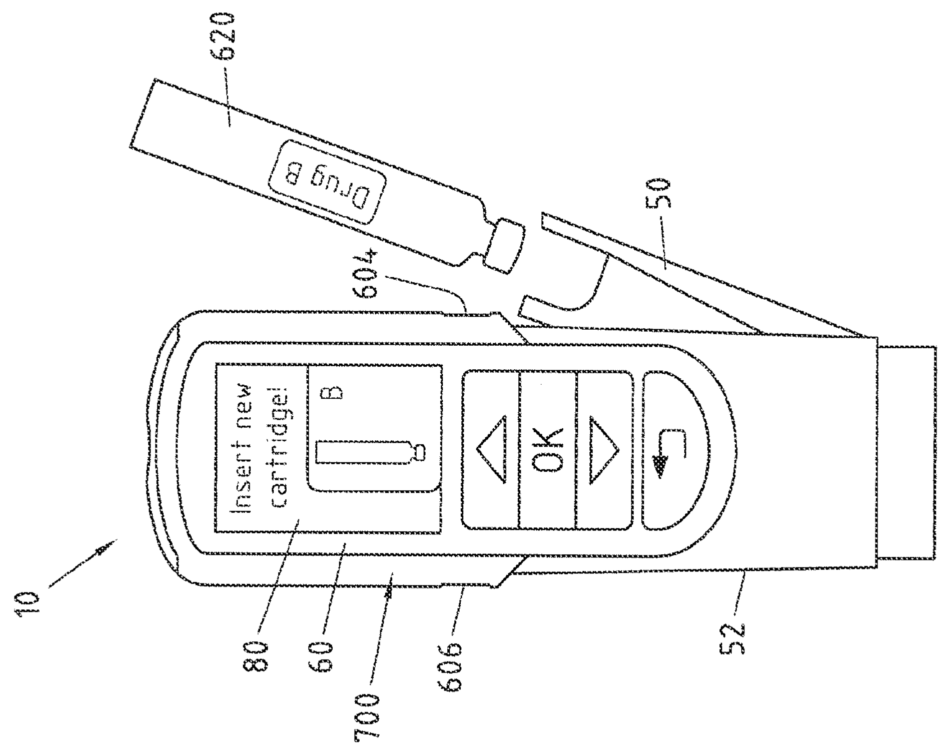
FIG. 13*b* illustrates a plan view of the medical delivery device with a second cartridge retainer in an open position.
Figure 13A:
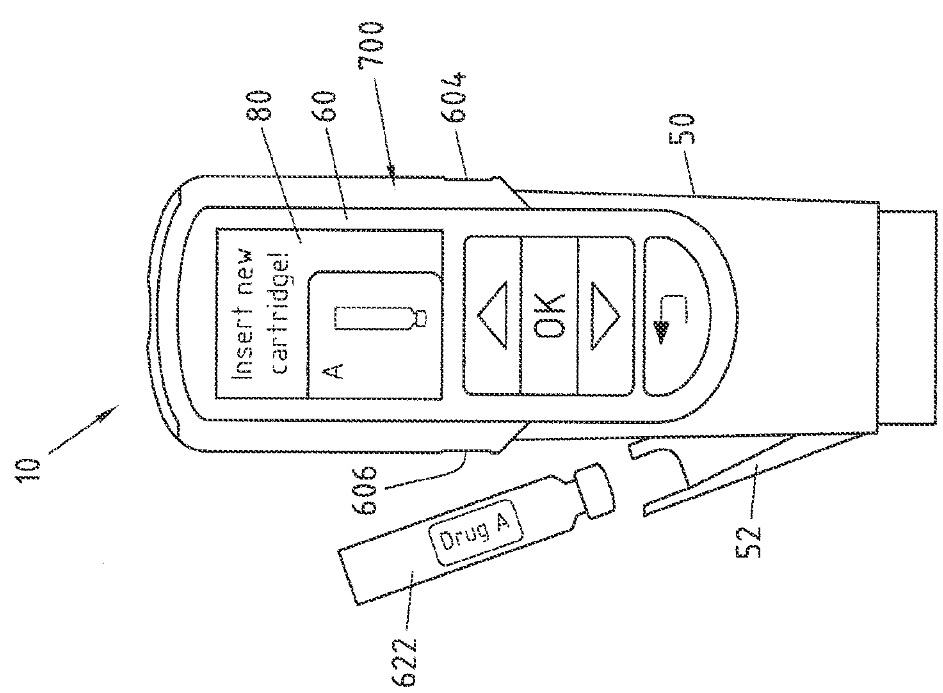
FIG. 13*a* illustrates a plan view of the medical delivery device with a first cartridge retainer in an open position.

FIG. 13*a* shows the medical device 10 in an open condition of cartridge retainer 52. In this condition the cartridge retainer 50 is in a closed position and also not openable. Accordingly, the latch 600 associated to the cartridge retainer 50 is in a locked condition and may not be unlocked by operating the respective cartridge release button 604. The latch 600 may be operated into the not-unlockable condition by the control device 700.

Likewise it is conceivable that the cartridge retainer 50 is locked by opening the cartridge retainer 52. In this case the locking condition of cartridge retainer 50 is only temporary and the cartridge retainer 50 is unlocked as soon as cartridge retainer 52 is moved back into the closed position.

Furthermore, as may be seen in FIG. 13*a*, the digital display 80 indicates instructions to the user of the medical device. Here, the cartridge retainer 52 is configured to receive a cartridge 622 filled with a drug A, which cartridge 622 has a small diameter and a short length. Accordingly, the digital display indicates to insert a cartridge retainer with a small diameter and a short length and which is filled with drug A into the opened retainer 52. In an example embodiment, the display 80 is a colour display that further shows a colour or a colour pattern associated with cartridge 622 or drug A. For example, the display may show the same colour or colour pattern that is shown on a label of cartridge 622. The display may also show the colour of a cartridge body, a ferrule and/or a bung or piston of the cartridge 622 containing drug A.

FIG. 13*b* shows the medical device 10 in an open condition of cartridge retainer 50. In this condition the cartridge retainer 52 is in a closed position and not openable. Accordingly, the latch 602 associated to the cartridge retainer 52 is in a locked condition and may not be unlocked by operating the respective cartridge release button 606. The latch 602 may be operated into the not-unlockable condition by the control device 700.

Likewise it is conceivable that the cartridge retainer 52 is locked by opening the cartridge retainer 50. In this case the locking condition of cartridge retainer 52 is only temporarily and the cartridge retainer 52 is unlocked as soon as cartridge retainer 50 is moved back into the closed position.

As may likewise be seen in FIG. 13*b*, the digital display 80 indicates instructions to the user of the medical device. The cartridge retainer 50 is configured to receive a cartridge 620 filled with a drug B, which cartridge 620 has a big diameter and a great length. Accordingly, the digital display indicates to insert a cartridge with a big diameter and a great length and which is filled with drug B into the opened retainer 50. Further, as described in relation to FIG. 13*a*, the display 80 may show a colour or a colour pattern shown on or on a label of cartridge 620 or associated with drug B.

Figure 14:
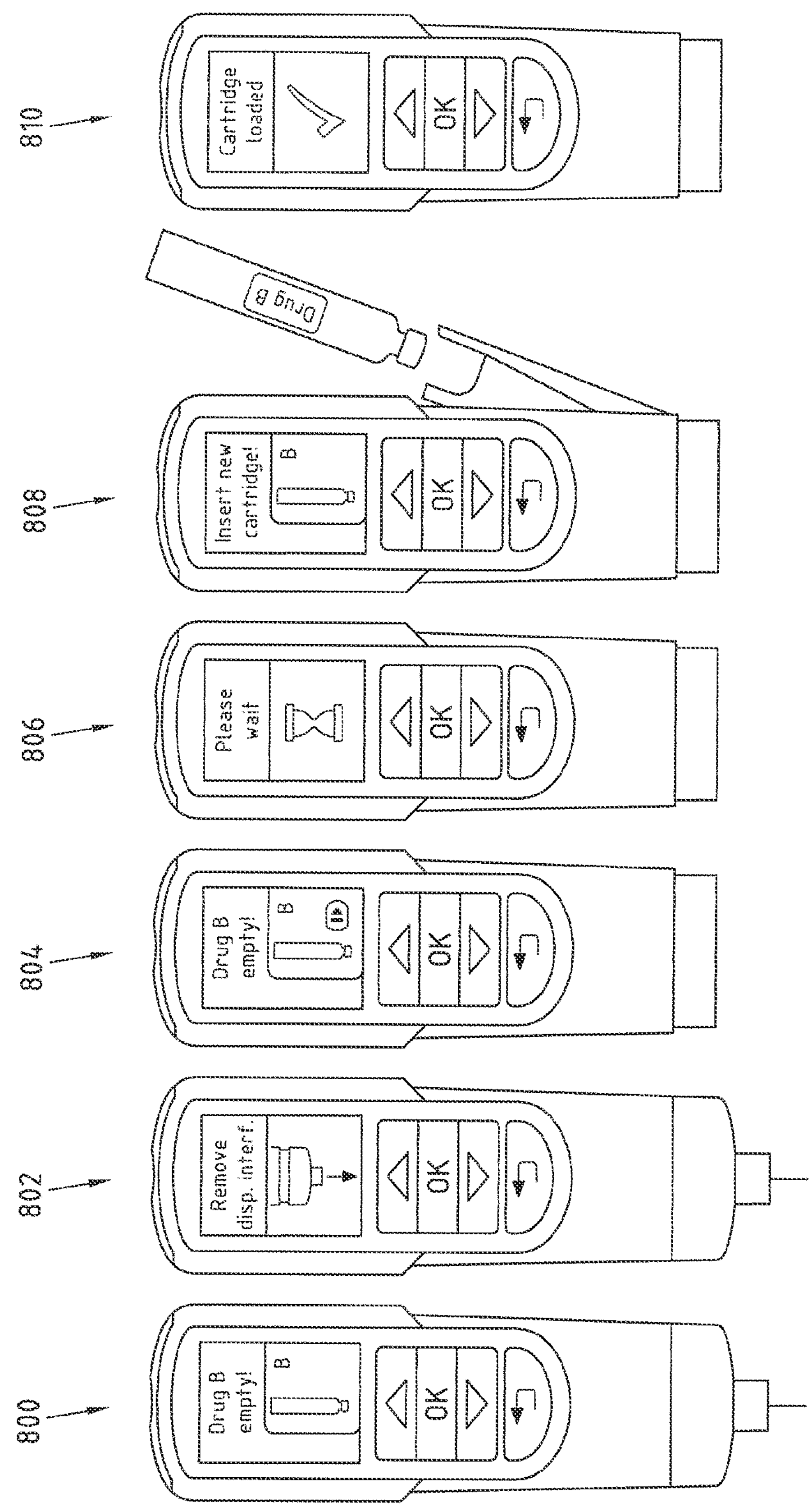
FIG. 14 illustrates a process for exchanging a medicament reservoir in the medical delivery device.

FIG. 14 illustrates a process of exchanging a cartridge in a medical delivery device 10. In step 800 the control device 700 of the medical device 10 determines, that the cartridge in retainer 50, is empty. Accordingly, the digital display 80 indicates that drug B is empty. Likewise in step 800 the digital display 80 illustrates a cartridge which has a big diameter and a great length.

Furthermore, in step 802 the digital display 80 indicates to remove the dispense interface 200. The indications on the digital display 80 shown in steps 800 and 802 may alternate during a certain period. Subsequently, the dispense interface 200 is removed from the cartridge holder 40 in step 802.

In step 804 the control device 700 determines the dispense interface 200 being removed from the cartridge holder 40. Further in step 804 the control device 700 may operate the locking device 600 into an unlockable condition, in case they have been in a not-unlockable condition while the dispense interface 200 has been attached to the cartridge holder 40. For example, the locking device 600 has been in a not-unlockable position because a piston rod is partly positioned inside the cartridge 620 and configured to press the bung of the cartridge during medicament administration. Thus, operating the locking device 600 into an unlockable condition may comprise retracting the respective piston rod inside the main housing.

Alternatively, retracting the piston rod may be done at any time after detecting an empty cartridge and before operating the locking device 600 into an unlockable condition.

Further, the digital display 80 indicates to operate the cartridge release button 604, whereby the locking device 600 may be unlocked or released.

Further in step 806 the cartridge release button 604 is operated. Thereby an according signal is send to the control device 700 which subsequently operates the locking devices

600 into a released or unlocked condition. At the same time locking device 602 is operated into a not-unlockable condition, in case this has not been conducted before.

In step 808 the cartridge retainer 50 is pushed out of the closed position into the open position, for example by the cartridge retainer spring 608. It is also possible that cartridge retainer 50 is pulled out into the open position by the user, without the aid of elastic spring forces. As soon as the cartridge retainer 50 has been opened, the detection switch 616 sends an according signal to the control device 700. The digital display 80 subsequently indicates to insert a new cartridge 622, filled with drug B, and illustrates a cartridge which has a big diameter and a great length.

In case an empty cartridge is present in cartridge retainer 50, this cartridge is now removed from the retainer 50. The new cartridge, which is filled with drug B, is then inserted into the cartridge retainer 50.

In the subsequent step 810 the cartridge retainer 50 is manually moved into the closed position, where it is locked by the locking device 600. In the closed position the detection switch 616 sends a corresponding signal to the control device 700, which may then operate the locking devices into an openable condition. The insertion condition of the inserted cartridge may furthermore be indicated on the digital display 80. In case the cartridge has correctly been inserted into the retainer 50 and the retainer 50 has also been closed properly, the dispense interface 200 may be reattached to the cartridge holder 40, whereby the medical device 10 will be operable again.

Opening and closing of the cartridge retainer 50 may also be operated by a motor or may be assisted by a motor, for example after detection of a button press of release button 604 or after detection of a press on the cartridge door or retainer, for example by a further switch or sensor.

The process illustrated in FIG. 14 and described precedent for the exchange of a cartridge in the cartridge retainer 50 is accordingly applicable for the exchange of a cartridge in cartridge retainer 52.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38[Asp28] Exendin-4(1-39)-NH2,
H-Asn-(Glu)5des Pro36, Pro37, Pro38[Asp28] Exendin-4(1-39)-NH2,
des Pro36, Pro37, Pro38[Asp28] Exendin-4(1-39)-(Lys)6-NH2,
H-(Lys)6-des Pro36, Pro37, Pro38[Asp28] Exendin-4(1-39)-(Lys)6-NH2,
H-Asn-(Glu)5-des Pro36, Pro37, Pro38[Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38[Trp(O2)25] Exendin-4(1-39)-NH2,
H-(Lys)6-des Pro36, Pro37, Pro38[Trp(O2)25, Asp28] Exendin-4(1-39)-NH2,
H-Asn-(Glu)5-des Pro36, Pro37, Pro38[Trp(O2)25, Asp28] Exendin-4(1-39)-NH2, des Pro36, Pro37, Pro38[Trp(O2)25, Asp28] Exendin-4(1-39)-(Lys)6-NH2, H-(Lys)6-des Pro36, Pro37, Pro38[Trp(O2)25, Asp28] Exendin-4(1-39)-(Lys)6-NH2, H-Asn-(Glu)5-des Pro36, Pro37, Pro38[Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38[Met(O)14, Asp28] Exendin-4(1-39)-NH2, H-Asn-(Glu)5-des Pro36, Pro37, Pro38[Met(O)14, Asp28] Exendin-4(1-39)-NH2, des Pro36, Pro37, Pro38[Met(O)14, Asp28] Exendin-4(1-39)-(Lys)6-NH2, H-(Lys)6-des Pro36, Pro37, Pro38[Met(O)14, Asp28] Exendin-4(1-39)-(Lys)6-NH2, H-Asn-(Glu)5 des Pro36, Pro37, Pro38[Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38[Met(O)14, Trp(O2)25] Exendin-4(1-39)-NH2, H-(Lys)6-des Pro36, Pro37, Pro38[Met(O)14, Asp28] Exendin-4(1-39)-NH2, H-Asn-(Glu)5-des Pro36, Pro37, Pro38[Met(O)14, Trp(O2)25, Asp28] Exendin-4(1-39)-NH2, des Pro36, Pro37, Pro38[Met(O)14, Trp(O2)25, Asp28] Exendin-4(1-39)-(Lys)6-NH2, H-(Lys)6-des Pro36, Pro37, Pro38[Met(O)14, Trp(O2)25, Asp28] Exendin-4(S1-39)-(Lys)6-NH2, H-Asn-(Glu)5-des Pro36, Pro37, Pro38[Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A cartridge holder, comprising:

a first cartridge retainer, at least a second cartridge retainer and a locking device for each cartridge retainer, wherein each cartridge retainer is configured to receive a medicament reservoir and wherein each cartridge retainer is movable between a closed and an open position, wherein the locking devices are configured to lock and unlock the cartridge retainers in the closed position and wherein the locking devices are configured to operate such that only one of the cartridge retainers at a time is movable into the open position.

2. The cartridge holder according to claim 1, wherein the locking devices are configured to operate between an openable condition, in which the respective cartridge retainer is movable into the open position, and a not-openable condition, in which the respective cartridge retainer is not movable into the open position.

3. The cartridge holder according to claim 2, wherein the locking devices are locked and unlockable in the openable condition and locked and not-unlockable in the not-openable condition.

4. The cartridge holder according to claim 2, wherein the locking devices are unlocked in the openable condition and locked in the not-openable condition.

5. The cartridge holder according to claim 2, wherein the locking devices are configured to operate from the openable into the not-openable condition and vice versa dependent on the positions of the cartridge retainers.

6. The cartridge holder according to claim 5, wherein the locking devices are configured to operate in the openable condition when all cartridge retainers are in the closed position.

7. The cartridge holder according to claim 5, wherein the locking devices are configured to operate such that when one of the cartridge retainers is moved into the open position, the locking devices associated to the remaining cartridge retainers operate in the not-openable condition.

8. The cartridge holder according to claim 1, further comprising a control device, which is configured to determine the positions of the cartridge retainers.

9. The cartridge holder according to claim 1, further comprising a control device which is configured to operate the locking devices dependant on the position of the cartridge retainers.

10. The cartridge holder according to claim 1, further comprising a control device, wherein the control device is an electronic control unit.

11. The cartridge holder according to claim 1, wherein the first cartridge retainer is configured for receiving medicament reservoirs of different sizes and/or different geometrical shapes than the at least second cartridge retainer.

12. The cartridge holder according to claim 1, wherein the cartridge retainers are hinged to a cartridge housing and rotatable between the closed and the open position.

13. An apparatus, comprising a main body and a cartridge holder according to claim 1, wherein the cartridge holder is removably attached to the main body.

14. A method for inserting of a medicament reservoir in a cartridge holder according to claim 1 comprising the following steps:

determining that a cartridge retainer is opened, operating the locking devices associated to the remaining cartridge retainers into a not-openable condition, determining that the opened cartridge retainer is closed, and operating the locking devices associated to the remaining cartridge retainers into an openable condition.

15. The method according to claim 14, further comprising:

determining that a medicament reservoir is inserted in the closed reservoir.

* * * * *